United States Patent
Heindl

(10) Patent No.: US 8,153,779 B2
(45) Date of Patent: Apr. 10, 2012

(54) NUCLEOTIDE WITH AN ALPHA-PHOSPHATE MIMETIC

(75) Inventor: Dieter Heindl, Paehl (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 228 days.

(21) Appl. No.: 12/580,445

(22) Filed: Oct. 16, 2009

(65) Prior Publication Data

US 2010/0093990 A1    Apr. 15, 2010

Related U.S. Application Data

(63) Continuation of application No. PCT/EP2008/003020, filed on Apr. 16, 2008.

(30) Foreign Application Priority Data

Apr. 18, 2007  (EP) .................................. 07007849

(51) Int. Cl.
C07H 19/10 (2006.01)
C07H 19/20 (2006.01)

(52) U.S. Cl. .................................. 536/26.23; 536/26.26

(58) Field of Classification Search .................. None
See application file for complete search history.

(56) References Cited

U.S. PATENT DOCUMENTS

| 5,587,361 | A | 12/1996 | Cook et al. |
| 6,210,891 | B1 | 4/2001 | Nyren et al. |
| 6,258,568 | B1 | 7/2001 | Nyren |

FOREIGN PATENT DOCUMENTS

| DE | 19650252 C2 | 1/2002 |
| EP | 1801114 A1 | 6/2007 |
| JP | 1224392 A | 9/1989 |
| WO | 02/46468 A3 | 6/2002 |
| WO | 03/008432 A1 | 1/2003 |
| WO | 03/027258 A3 | 4/2003 |
| WO | 03/050290 A3 | 6/2003 |
| WO | 2005/054431 A3 | 6/2005 |
| WO | 2007/059816 A1 | 5/2007 |

OTHER PUBLICATIONS

International Search Report issued Aug. 13, 2008 in PCT Application No. PCT/EP2008/003020.
International Preliminary Report on Patentability issued Oct. 20, 2009 in PCT Application No. PCT/EP2008/003020.
Baschang, Gerhard and Kvita, Vratislav, "Imidophosphate als neue Nucleotid-Derivate," Angewandte Chemie, 1973, pp. 43-44, vol. 85, No. 1.
Bräse, Stefan et al., "Organische Azide-explodierende Vielfalt bei einer einzigartigen Sbustanzklasse," Angewandte Chemie, 2005, pp. 5320-5374, vol. 117.
Burgess, Kevin and Cook, Dan, "Syntheses of Nucleoside Triphosphates," Chemical Reviews, 2000, pp. 2047-2059, vol. 100.
Ghadessy, Farid J. and Holliger, Philipp, "Compartmentalized Self-Replication a Novel Method for the Directed Evolution of Polymerases and Other Enzymes," Methods in Molecular Biology, 2007, pp. 237-248, vol. 352.
Graham, Steven M. and Pope, Sarah C., "Selective Phosphitylation of the Primary Hydroxyl Group in Unprotected Carbohydrates and Nucleosides," Organic Letters, 1999, pp. 733-736, vol. 1, No. 5.
Hansch, Corwin et al., "A Survey of Hammett Substituent Constants and Resonance and Field Parameters," Chemical Reviews, 1991, pp. 165-195, vol. 91.
Ludwig, János and Eckstein, Fritz, "Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphosphorin-4-one," Journal of Organic Chemistry, 1989, pp. 631-635, vol. 54.
McMurry, John E. and Coppolino, Anthony P., "The Cyanogen Azide Ring-Expansion Reaction," Journal of Organic Chemistry, 1973, pp. 2821-2827, vol. 38, No. 16.
Misiura, Konrad et al., "Synthesis of Nucleoside α-Thiotriphosphates via an Oxathiaphospholane Approach," Organic Letters, 2005, pp. 2217-2220, vol. 7, No. 11.
Nielsen, John and Caruthers, Marvin H., "Directed Arbuzov-Type Reactions of 2-Cyano-1,1-dimenthylethyl Deosynucleoside Phosphites," Journal of the American Chemical Society, 1988, pp. 6275-6276, vol. 110.
Simoncsits, A. and Tomasz, J., "A New Type of Nucleoside 5'-Triphosphate Analogue: P1-(Nucleoside 5'-) P1-Amino-Triphosphates," Tetrahedron Letters, 1976, pp. 3995-3998, No. 44.
Tomasz, Jeno et al., "5'-P-Borane-Substituted Thymidine Monophosphate and Triphosphate," Angewandte Chemie International Edition in English, 1992, pp. 1373-1375, vol. 31, No. 10.
Wagner, Thomas and Pfleiderer, Wolfgang, "An Inverse Approach in Oligodeoxyribonucleotide Synthesis," Nucleosides & Nucleotides, 1997, pp. 1657-1660, vol. 16, Nos. 7-9.
Zhu, Shi-Zheng et al., "Reactions of Fluoroalkanesulfonyl Azides with Diethyl Phosphite, A New Method for the Synthesis of N-Fluoroalkanesulfonylphosphoramidates," Chinese Journal of Chemistry, 2001, pp. 1259-1262, vol. 19.

*Primary Examiner* — Lawrence E Crane

(57) ABSTRACT

Described are modified mononucleotides and processes for their production. The nucleotides have a structure

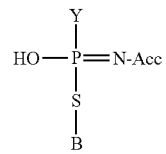

in which B is a purine or pyrimidine, S is a sugar unit, Y is an OH, a monophosphate, or a diphosphate, and Acc is an electron acceptor selected from the group consisting of (a) —CN and (b) —SO$_2$—R' in which R' contains one amino-substituted alkyl or one optionally substituted aryl.

5 Claims, No Drawings

NUCLEOTIDE WITH AN ALPHA-PHOSPHATE MIMETIC

RELATED APPLICATIONS

This application is a continuation of PCT/EP2008/003020 filed Apr. 16, 2008 and claims priority to EP 07007849.8 filed Apr. 18, 2007.

FIELD OF THE INVENTION

The present invention concerns new substances and processes for producing them in the field of nucleotide chemistry. These substances are so-called phosphate mimetics in which an oxygen atom is replaced by a corresponding mimetic.

In particular the present invention concerns a new class of nucleotides with a modified alpha-phosphate and in particular triphosphate nucleotides and processes for producing them.

BACKGROUND

Various processes for producing nucleotides modified on the phosphate residue have already been described in the past. A review of currently used techniques to synthesize nucleoside triphosphates (NTP) may be found in Burgess, K., and Cook, D., Chem. Rev. 100 (2000) 2047-2059 and a review especially of NTPs with a modified triphosphate side chain may be found in Koukhareva, Vaghefi and Lebedev, Nucleoside Triphosphates and their Analogs (2005) Chapter 2, "Synthesis and properties of NTP analogs with modified Triphosphate side chains", Ed. M. Vaghefi, CRC Press, Taylor & Francis, Boca Raton. Triphosphates are of outstanding importance especially because, after cleavage of the pyrophosphate, they are incorporated as monophosphate substrates into long chain nucleic acids by DNA or RNA polymerases. Usually nowadays nucleoside monophosphates are firstly prepared which are subsequently enzymatically converted into triphosphates for example by kinases.

Modified nucleoside triphosphates are advantageous for various applications such as for example the preparation of aptamers (WO 03/50290) or antisense molecules (U.S. Pat. No. 5,587,361) and they are also used in sequencing (WO 02/46468) and PCR (WO 03/27258). Use of alpha-thio-dATP as a substrate for pyrosequencing reactions has become particularly important (WO 05/54431).

Alpha-phosphate-modified nucleoside triphosphates such as for example alpha thio-triphosphates or alpha-amino NTPs (Simoncsits, A., Tomasz, J., A new type of nucleoside 5'-triphosphate analog: P1-(nucleoside 5'-) P1-aminotriphosphates. Tetrahedron Letters 17(44) (1976) 3995-8) have been known for a long time. The preparation of alpha-methyl phosphonates (JP 01224392) and alpha-borano phosphates (Tomasz, J., et al., 5'-P-borane-substituted thymidine phosphate and triphosphate, Angewandte Chemie 104(10) (1992) 1404-6; Tomasz, J., et al., Angew. Chemie 31(10) (1992) 1373-5) has also already been described. WO 03/008432 describes the separation of N-alkyl-substituted derivatives by treating nucleotidyl-cyclo-triphosphite with an oxidizing agent in the presence of amines.

The preparation of modified nucleotide esters with the aid of azides is also known from the prior art. Baschang and Kvita, Angewandte Chemie 85(1) (1973) 43-44 describe the reaction of a nucleotide phosphoric acid triester with azides such as methyl-sulfonyl azide to prepare trialkyl(aryl)-imidophosphates. However, they are unstable and decay.

Nielsen, J., and Caruthers, M. H., J. Am. Chem. Soc. 110 (1988) 6275-6276 describe the reaction of deoxynucleoside phosphites provided with a 2-cyano-1,1-dimethylethyl protecting group in the presence of alkyl azide. In addition the authors suggest that this principle is suitable for preparing oligonucleotides with a modified inter-nucleoside phosphate without elucidating which types of modifications prepared with the aid of the disclosed process could have special advantages. In particular the authors propose introducing alkyl residues into oligonucleotides during oligo-nucleotide synthesis. Nucleoside triphosphates are not a subject matter of this publication.

Thus, all these publications describe the preparation of molecules which contain a phosphoramidite instead of a phosphate residue. However, molecules containing phosphoramidites are subject to hydrolysis because the amine group is protonated in an acidic medium and is then substituted by water. Consequently the previously described methods are of only very limited suitability for producing stable alpha-phosphate-modified nucleotides.

The technical object forming the basis of the present invention was thus to provide improved nucleotides modified on the alpha-phosphate, so-called alpha-phosphate mimetics, and to provide simple processes for their production.

SUMMARY OF THE INVENTION

The present invention concerns a nucleotide of the structure

X—S—B in which B is a naturally occurring nucleobase, a modified nucleobase or a nucleobase analogue,
S is a sugar unit,
X is a mono-, bis- or triphosphate,
characterized in that an oxygen atom of the alpha-phosphate is replaced by

in which Acc is an electron acceptor or an electron acceptor substituted with a residue R and R is any organic substituent.

Acc is preferably selected from a group comprising
a) —CN,
b) —SO$_2$—R' in which R' contains at least one amino-substituted alkyl, an optionally substituted aryl or an optionally substituted heterocycle,
c) and electron-deficient, six-membered N$^+$-heterocycles in which at least one nitrogen atom is alkylated and is in an ortho or para position and wherein these heterocycles can be optionally substituted with R.

In this connection R or R' can contain a detectable unit or a functional group. Acc or the SO$_2$ group can be an integral part of said detectable unit or said functional group.

The sugar unit is in particular a ribose, deoxyribose or dideoxyribose.

The 3' position of the nucleotide according to the invention is preferably selected from a group comprising H, OH, a protective group, a label, a mononucleotide, a polynucleotide or a solid phase.

The present invention also concerns a process for producing a nucleotide modified at the alpha position which is characterized in that
a trivalent phosphorus atom located at the 5' position of a nucleotide and provided with at least one protected hydroxyl group is reacted with an azide of the structure

in which Acc is an electron acceptor or an electron receptor substituted with a residue R and R is any organic substituent.

Acc is preferably selected from a group comprising
a) —CN, —SO$_2$—R'
b) and electron-deficient, six-membered N$^+$-heterocycles in which at least one nitrogen atom is alkylated and is in an ortho or para position and wherein these heterocycles can be optionally substituted with R.

The present invention in particular also concerns a process in which a 5'-phosphoric acid di-ester nucleoside is reacted with an azide of the structure

in which Acc is an electron acceptor or an electron receptor substituted with a residue R and R is any organic substituent.

Furthermore, the present invention concerns the use of a nucleotide according to the invention as a substrate of a polymerase-catalysed nucleic acid synthesis in particular for the synthesis of a modified nucleic acid.

The present invention additionally concerns the use of a nucleotide according to the invention as a substrate in a pyrophosphate sequencing reaction.

DETAILED DESCRIPTION OF THE INVENTION

Basic Idea of the Invention

The aim of the present invention is to produce nucleotides in a simple manner which contain alpha-phosphate-modified phosphate residues and thus can preferably also contain detectable labels.

The core idea of the present invention was, in this connection, firstly to start with a trivalent phosphorus atom of a nucleotide and to react it with a reagent in such a manner that a stable phosphate mimetic is formed. For this purpose according to the invention a phosphorus atom containing at least one hydroxyl residue which is provided with a protective group is reacted with an azide of the structure N=N=N-Acc, in which Acc is an electron acceptor or an electron receptor substituted with a residue R and R is any organic substituent. This results in the formation of a pentavalent phosphorus atom which is covalently bound via an N atom to a strong electron-attracting electron acceptor group. This group ensures that the compounds prepared in this manner are, in contrast to the phosphoramidites known from the prior art, resonance-stabilized and are not subject to hydrolysis.

This idea on which the invention is based can be applied to all methods in which a trivalent phosphorus compound is formed as an intermediate of the synthesis.

DEFINITIONS

Some of the terms used within the scope of the present invention are defined as follows:

Groups of a molecule are referred to as reactive groups which are able under suitable conditions to react with another molecule to form a covalent bond. Examples of reactive groups are hydroxyl groups, amino groups, thiol, hydrazino, hydroxylamino, dienes, alkines and carboxylic acid groups.

Protective groups refer to molecules which react with one or more reactive groups of a molecule such that only one particular, non-protected reactive group can react with the desired reaction partner in a multistep synthesis reaction. Examples of frequently used protective groups for protecting hydroxyl groups are beta-cyano-ethyl, methyl, trialkylsilyl and allyl protective groups. Protective groups for protecting amino groups are trifluoroacetyl and Fmoc. Other possible protective groups are summarized in standard works (Greene, T. W., Protective groups in organic synthesis (1981) Wiley Interscience Publications, John Wiley & Sons, New York, Chichester, Brisbane Toronto; Sonveaux, E., in Methods in Mol. Biology 26 (1993) chapter 1, Protocols for Oligonucleotide Conjugates Humana Press, Totowa, N.J.).

Carbon chains having a length of 1-30 C atoms are referred to as linkers. Such linker chains can additionally have one or more nitrogen, oxygen, sulphur and/or phosphorus atoms. Moreover, linkers can also be branched e.g. also be dendritic.

A detectable unit is understood as substances which can be detected with the aid of analytical methods. They can for example be units or substances that can be detected mass spectroscopically, immunologically or with the aid of NMR. Detectable units are in particular also substances that can be detected by optical methods such as fluorescence and UV/VIS spectroscopy such as for example fluoresceins, rhodamines or also gold particles. They also include intercalators and minor groove binders which at the same time have an effect on the melting behaviour and change their fluorescence by hybridization.

The term "nucleoside triphosphates" (NTP) subsumes in connection with the present invention not only the natural (deoxy) nucleoside triphosphates but also NTPs which in addition to the modification according to the invention can also have additional modifications on the triphosphate side chain (such as for example methyl phosphonates, phosphothioates). Furthermore, they can also contain modified sugars or sugar analogues (such as e.g. 2'-O-alkyl derivatives 3' and/or 5' aminoribose, locked ribose, hexitol, altritol, cyclohexene, cyclopentane) or modified bases such as for example 5 methyl C or base analogues such as e.g. 7-deazapurines. The base, the sugar or the triphosphate side chain of such NTPs can be linked via a linker with a detectable unit or reactive group.

The term "oligonucleotide" subsumes in connection with the present invention not only (deoxy) oligoribonucleotides but also oligonucleotides which contain one or more nucleotide analogues with modifications on the phosphate backbone (such as for example methylphosphonates, phosphothioates) on the sugar (such as for example 2'-O-alkyl derivatives 3' and/or 5' aminoribose, LNA, HNA, TCA) or modified bases such as 7-deazapurines.

The term "electron acceptor" encompasses atomic structures which have a tendency to bind free electron pairs. A measure for this is the Hammet constant. The present invention concerns in particular embodiments in which the Hammet constant $\sigma_p()$ exceeds a certain value of 0.30, preferably 0.45 and most preferably 0.60.

Examples of electron acceptors which fulfil these conditions are:
—NO$_2$, —SO$_2$—R, —CN, —CO—R, pyrimidinyl, pyridinyl, pyridazinyl, hexafluorophenyl, benzo-triazolyl, e.c. (Hansch, C., et al., Chem. Reviews 91 (1991) 165-195). Moreover, these acceptors can also be bound in a vinylogous or phenylogous manner to the nitrogen atom.

The term "substituted" means that the structure which is in each case referred to as substituted contains a further residue at any position provided this position is not defined in more detail. The term "optionally substituted" means that the structure that is referred to comprises embodiments with and without an additional residue.

The term "amino-substituted alkyl" encompasses C$_1$-C$_{30}$ linear or branched alkyl which contains at least one amino group wherein this amino group is protected or is connected via a linker to a detectable unit.

The term "electron-deficient, six-membered N$^+$ heterocycle" includes N heterocycles which are alkylated on an sp2 nitrogen so that the charge of the heterocycle is overall positive. Examples of this are pyridinium, pyrimidinium and quinolinium.

The term "nucleobase" refers to the entirety of all purines and pyrimidines and their derivatives and analogues.

The term "alpha-phosphate" refers to the phosphate atom which is directly covalently bound to the 5' C atom of the ribose unit of the nucleoside.

Nucleotides According to the Invention

The present invention concerns a nucleotide of the structure

X is a mono-, bis- or triphosphate
B can be a naturally occurring nucleobase such as adenine, guanine, cytosine, thymidine or uridine. B is alternatively a modified nucleobase such as for example 5-aminoallyl uridine or N6-[(2-biotinylamido)ethyl]-adenosine or a nucleobase analogue such as for example 7-deaza guanosine or etheno-adenosine.
S is a sugar unit. In particular the sugar unit is a ribose, deoxyribose or dideoxy-ribose. S is preferably a single sugar unit such as for example a single ribose, deoxy-ribose or dideoxyribose.

The 2' and/or 3' position of the ribose is preferably selected from a group comprising H, OH, phosphate, a protective group, a label, a mononucleotide, a polynucleotide or a solid phase. If the 2' and 3' positions carry a hydroxyl group, then it is consequently a ribonucleotide which can be enzymatically incorporated in the form of a triphosphate into RNA by RNA polymerases. If a hydroxyl group is at the 3' position and a hydrogen atom is at the 2' position, then it is a deoxyribonucleotide which can be incorporated into DNA in the form of a triphosphate by DNA polymerases. Examples of such DNA polymerases are reverse transcriptases such as AMV-RT, Klenow polymerase or polymerases suitable for PCR such as Taq DNA polymerase.

However, the present invention also concerns oligonucleotide triphosphates in which the 3' position of the ribose is bound to at least one further nucleotide residue. In another embodiment the ribose can be bound either directly or via an appropriate molecular linker to a solid phase such as for example a microtitre plate surface or a particle. Examples of such particles are so-called magnetic beads or glass beads. Furthermore the 3' or 2' position of the ribose can be linked with a detectable unit. Alternatively S is a modified sugar such as e.g. 2' fluororibose or a ribose analogue such as for example hexitol. X is a mono-, bis- or triphosphate and is characterized in that an oxygen atom of the alpha-phosphate is replaced by —N-Acc.

Preferably, the molecules according to the invention have the structure

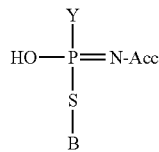

in which B represents a nucleobase and S represents a sugar unit and
Y represents either OH or a monophosphate or a diphosphate. Acc is an electron acceptor or an electron acceptor substituted with a residue R. R is any organic substituent.

In a first variant of the invention Acc is a cyano group —CN.

In a second embodiment Acc is an electron-deficient, six-membered N+ heterocycle in which at least one nitrogen atom is alkylated and is located in the ortho or para position. These heterocycles can be optionally substituted with any residue R. These heterocycles are in particular pyridinium, pyrimidinium or quinolinium.

In a preferred embodiment Acc is —SO₂—R', in which R' contains at least one amino-substituted C1-C12 alkyl, an optionally substituted aryl or an optionally substituted heterocycle.

In this connection R or R' can contain a detectable unit or a functional group. Acc or the SO₂ group can be an integral part of said detectable unit or said functional group.

Hence the invention also concerns embodiments of —SO₂—R', in which R' as such is an amino-substituted C1-C12 alkyl, an optionally substituted aryl or an optionally substituted heterocycle. However, all electron acceptors are of special interest which can contain any organic residue because the methods of synthesis described within the scope of this application thus enable the simple preparation of nucleotides modified with any organic residues.

Thus the present invention in particular also concerns nucleotides in which an electron acceptor substituted with the residue R contains a detectable unit as R or alternatively a functional group as R to which a detectable unit can be coupled.

Alternatively the present invention also encompasses embodiments in which the electron acceptor is a component of the detectable unit. Alternatively the residues R or R' can as such represent the detectable unit or functional group.

Hence, the detectable label is preferably a fluorescent dye or a fluorescence quencher molecule. Appropriate dyes or molecules which can be used as a detectable unit for example in sequencing are well-known to a person skilled in the art. Examples of these which do not limit the protective scope of the present invention are: fluoresceins, rhodamines, cyanins, merocyanins, carbocyanins and azo and polyazo compounds.

Production of the Nucleotides According to the Invention

The present invention also concerns a process for producing a nucleotide modified at the alpha-position which is characterized in that a trivalent phosphorus atom provided with at least one protected hydroxyl group and located at the 5' position of a nucleotide is reacted with an azide of the structure

with cleavage of nitrogen, in which Acc is an electron acceptor or an electron acceptor substituted with a residue R and R is any organic substituent.

The following come into consideration as protective groups for the hydroxyl group of the trivalent phosphorus: beta-cyanoethyl, methyl, trialkylsilyl and allyl.

Azides substituted with electron acceptors are known to a person skilled in the art from the literature; some are commercially available or can be prepared by simple syntheses. Acc-azides such as e.g. acyl azides and sulphonyl azides can be prepared from acyl or sulphonyl chlorides using sodium azides or from hydrazides using nitrous acid (Review: Bräse, S., et al., Angewandte Chemie 117 (2005) 5320-5374, 3.4 and 3.5.2).

Dye sulphonyl azides are for example also used in dyeing processes (e.g. DE 196 50 252). Cyanogen azide can be simply prepared by reacting sodium azide with bromocyanogen in acetonitrile (McMurry, J. E., et al., J. Organic Chemistry 38(16) (1973) 2821-7). Heteroaryl azides can be prepared by nucleophilic substitution of a halogen with azides or from heteroaryl hydrazines. A precondition is that the electron-attracting nitrogen is in the para or ortho position relative to the azido group because only then is a resonance-stabilized phosphate mimetic formed. In this connection ortho or para N-alkyl pyridinium azides are particularly suitable. Some acyl, sulphonyl and pyridyl azides are also commercially available.

Acc is preferably selected from a group comprising
a) —CN,
b) —SO$_2$—R
c) electron-deficient, six-membered N$^+$-heterocycles in which at least one nitrogen atom is alkylated and is in an ortho or para position and wherein these heterocycles can be optionally substituted with R.

Particularly preferred electron acceptors Acc have already been described in detail in the section "nucleotides according to the invention".

Initially mononucleotides with an alpha-phosphate mimetic are always produced according to the invention by this method of synthesis. Alpha-phosphate-modified nucleoside diphosphates and triphosphates can be prepared subsequently using methods that are basically known from the prior art. This is preferably carried out enzymatically. Firstly the monophosphate mimetic is reacted with ATP in the presence of an NMP kinase such as for example adenylate kinase to form an alpha-phosphate-modified diphosphate mimetic. In an additional step, this product can then be reacted with ATP in the presence of creatine kinase to form a corresponding alpha-phosphate-modified isomerically-pure triphosphate mimetic. Alternatively the triphosphate can be prepared chemically by condensation with pyrophosphate. Two diastereoisomers are formed in this process which can be separated by means of HPLC.

The present invention also especially concerns a method in which a 5' phosphoramidite nucleoside is reacted with an azide of the structure

in which Acc can be an electron acceptor according to the inventive alternatives described above.

Just like the 3' phosphoramidites used for conventional oligonucleotide synthesis, the 5' phosphoramidites used according to the invention are also commercially available (GlenResearch; 5' CE phosphoramidites). They are used for inverse oligonucleotide synthesis (Wagner, T., and Pfleiderer, W., Nucleosides & Nucleotides 16(7-9) (1997) 1657-1660). Furthermore, these molecules are also a suitable starting substance for preparing monophosphates with a modified alpha-phosphorus. For this purpose 5-cyanotheyl phosphoramidites of (deoxy) ribonucleosides are activated with tetrazole and reacted with an alcohol e.g. cyanoethanol. This results in the formation of a phosphonic acid triester having an ester bond to the nucleoside and two further ester bonds to protected hydroxyl groups. One of these is already present in the phosphoramidite, the other is introduced by the reaction with the alcohol. Subsequently the trivalent phosphorus intermediate is reacted with an azide of the structure N=N=N-Acc. Nitrogen is cleaved off in this process as a byproduct. The protective group on the hydroxyl group can for example be formed by beta-cyanoethyl, methyl, allyl or silyl and is subsequently cleaved off for example with ammonia.

Alternatively a phosphonic acid triester can also be directly prepared from the nucleoside by phosphytilation with bis(2-cyanoethyl)-N,N-diisopropylphosphor-amidite (Graham, S. M., and Pope, S. C., Organic Letters 1(5) (1999) 733-736). The phosphonic acid triester that is formed, is then reacted as described above with an azide and the cyanoethyl protective groups and the protective groups are cleaved off. The resulting monophosphate with a modified phosphorus can then be reacted enzymatically with the aid of kinases or with the aid of condensation reagents such as carbonyl diimidazole with phosphate or pyrophosphate to form a diphosphate or triphosphate.

Alternatively other nucleoside phosphites containing a trivalent phosphorus atom can also be used as starting substances. For this a protected nucleoside is phosphytilated with 2-chloro-4H-1,3,2-benzodiaoxaphosphorin-4-one. Subsequently it is reacted with pyrophosphate to form a cyclic triphosphite which is then reacted with an azide. Subsequent hydrolysis of the trimetaphosphate that is formed and cleavage of the protective groups yields the alpha-modified triphosphate (Ludwig, J., and Eckstein, F., Journal of Organic Chemistry 54(3) (1989) 631-35). This method was also applied to commercially available nucleosides immobilized on CPG (WO 03/008432) and can also be used to prepare oligo-nucleotide triphosphates. As an alternative to 2-chloro-4H-1,3,2-benzodioxa-phosphorin-4-one it is also possible to phosphitylate with oxathiophospholane (Misiura, K., Szymanowicz, D., Stec, W. J., Organic Letters 7(11) (2005) 2217-2220).

Other low-valency phosphorus precursors are H-phosphonates. These can also react with azides to form the monophosphates modified according to the invention (Zhu, S. Z., et al., Chinese Journal of Chemistry 19 (2001) 1259-1262).

Range of Application

The alpha-phosphate mimetic nucleotides and alpha-phosphate mimetic nucleoside mono-, di- or triphosphates according to the invention have a number of advantages compared to the modified alpha-amidates, alpha-thiophosphates and alpha-boranophosphates known from the prior art. Firstly the structures according to the invention are not oxidation-sensitive. In comparison to the amidates, the compounds according to the invention are also insensitive to hydrolysis and thus considerably more stable in aqueous solution. Moreover, in contrast to thiophosphates and boranophosphates, the compounds according to the invention are suitable for labelling nucleotides with detectable units because with the aid of an azide of the structure N=N=N—SO$_2$—R it is possible to couple almost any detectable unit to any nucleotide by a relatively simple method of synthesis.

Hence the present invention also concerns the use of a nucleotide triphosphate according to the invention as a substrate of a polymerase-catalysed nucleic acid synthesis.

In a first embodiment the nucleic acid synthesis is an in vitro transcription with the aid of an RNA polymerase such as for example T7 RNA polymerase or SP6 RNA polymerase in which ribonucleoside triphosphates according to the invention are incorporated into the nascent RNA. In this manner it is possible to produce large amounts of labelled RNA which can be used for analytical purposes such as array hybridization.

In a second embodiment the nucleic acid synthesis is a reverse transcriptase reaction in which deoxyribonucleoside triphosphates according to the invention are incorporated into cDNA that is synthesized with the aid of an RNA-dependent DNA polymerase such as for example AMV reverse transcriptase or thermostable polymerases having reverse transcriptase activity (for example T.th, Roche Applied Science Cat. No. 11 480 014 001). The labelled cDNA prepared in this manner can also be used as a hybridization probe for numerous analytical applications.

In a third embodiment the deoxyribonucleoside triphosphates according to the invention are incorporated into a DNA strand that has been newly synthesized with the aid of a DNA-dependent DNA polymerase such as Klenow polymerase. The labelled cDNA prepared in this manner can also be used as a hybridization probe for analytical applications.

The alpha-phosphate mimetic dNTPs according to the invention can also be advantageously used for sequencing methods. Thus the newly synthesized DNA strands can be labelled as part of a Sanger sequencing.

However, an alpha-phosphate mimetic dATP according to the invention is particularly advantageously used for pyrosequencing reactions. The principle of pyrosequencing is based on the fact that, after annealing a sequencing primer to the template DNA, the primer is extended with the aid of a DNA polymerase in which the four different deoxynucleoside triphosphates are sequentially added in multiple cycles. The pyrophosphate which is formed in each case as a byproduct of the reaction by incorporation of the monophosphate, is detected in a time-resolved manner by a reaction cascade. In this process sulphurylase catalyses the reaction of adenosine 5' phosphosulphate with the pyrophosphate that is formed to form ATP. Luciferin is then reacted with the aid of the ATP that is generated by the enzyme luciferase to form oxyluciferin resulting in a detectable chemiluminescence signal (U.S. Pat. No. 6,210,891, U.S. Pat. No. 6,258,568). It is necessary to use dATP analogues for the incorporation of adenosine residues into the nascent DNA because dATP like ATP is a co-substrate that is recognized by the luciferase and can consequently not be used for pyrosequencing.

However, the alpha-thio-dATP that is used according to the prior art is relatively unstable at room temperature and is thus only of limited suitability for use in sequencing reactions. Therefore, a subject matter of the present invention is in particular the use of an alpha-phosphate mimetic adenosine triphosphate according to the invention as a substrate in a pyrophosphate sequencing reaction. Embodiments have proven to be particularly suitable for this purpose in which the acceptor is sterically less demanding. Cyano and methylsulphonyl are especially suitable as an acceptor.

In the case of sterically more demanding residues, the polymerase can be modified for example by means of CSR to adapt it to the substrate (Ghadessy, F. J., and Holliger, P., Methods in Molecular Biology 352 (2007) 237-248 (Protein Engineering Protocols), (Totowa, N.J., United States), Compartmentalized self-replication: a novel method for the directed evolution of polymerases and other enzymes). This allows the enzymatic synthesis of aptamers with a high degree of diversity because any residues can be introduced on the alpha-phosphate.

The triphosphates according to the invention can also be used to enzymatically label oligonucleotides with the aid of terminal transferase. If the alpha-phosphate of dideoxy A,G,C,T is labelled in each case with different dyes, then such triphosphates can also be used for so-called dye terminator sequencing analogously to the previous base-labelled triphosphates.

The invention whose protective scope is derived from the patent claims is further elucidated by the following examples and publications. The described methods are to be understood as examples which still describe the subject matter of the invention even after modifications.

Example 1

Thymidine Monocyaniminomonophosphate 370 mg (0.5 mmol) 3'-dimethoxytriyl thymidine, 5'-[(2-cyanoethyl)-(N,N-diisopropyl)]-phosphoramidite (GlenResearch) is dissolved under argon in 2.5 ml anhydrous acetonitrile and firstly 2.2 ml of a 0.45 M solution of tetrazole in acetonitrile (Fluka) and then 150 µl (1.5 mmol) 3-hydroxypropionitrile are successively added. The reaction mixture is stirred for 20 minutes at room temperature and subsequently 1.56 ml of a 0.32 M solution of cyanogen azide in acetonitrile is added (cyanogen azide prepared according to: McMurry, J. E., et al., J. Organic Chemistry 38(16) (1973) 2821-7). After 30 minutes the solution is diluted with ethyl acetate and shaken out with water. The organic phase is dried with sodium sulphate and the solvent is evaporated on a rotary evaporator. 8 ml 7 N methanolic ammonia solution is added to the residue and allowed to stand for 5 hours at room temperature in a sealed vessel. The solvent is removed, water is added to the residue and the water is also removed. The oily residue is dissolved in 40 ml of an 80% acetic acid solution and stirred for 15 min at room temperature. The acetic acid is removed on a rotary evaporator. The residue is dissolved in 10 ml 37% aqueous ammonia, afterwards the ammonia is removed and the product is purified over a DEAE Sephadex A25 anion exchanger (eluant gradient: from 0.1 M ammonium acetate solution pH=7 in 120 minutes to 1 M ammonium acetate solution pH=7). Mass (ESI) M/e 347.1 (calculated $C_{11}H_{15}N_4O_7P$ 345.2), 1H NMR ($D_2O$, ppm) 7.76 (s, 1H), 6.34 (t, 1H), 4.42 (m, 1H), 4.16 (m, 1H), 4.04 (m, 2H), 2.36 (m, 2H), 1.94 (s, 3H), 31P NMR ($D_2O$, ppm) 1.5.

Example 2

Thymidine Monocyaniminotriphosphate (Enzymatic Synthesis)

2 mg thymidine monocyaniminomonophosphate is dissolved in 1 ml water and 4 mg creatine phosphate×$4H_2O$, 1 mg magnesium acetate×$4H_2O$ and 0.01 mg ATP are added. The pH is adjusted to 7.3 with a dilute sodium hydroxide solution and subsequently 1 mg creatine phosphokinase from hare muscle (EC 2.7.3.2) (185 U/mg) and 1 mg TMP kinase (EC 2.7.4.9) (32 U/mg) are added. It is all carefully stirred at 37° C. After 1 hour the enzymes are denatured for 15 minutes at 65° C., the solution is filtered and purified over a DEAE Sephadex A25 anion exchanger (eluant gradient: from 0.01 M ammonium acetate solution pH=7 in 120 minutes to 1 M ammonium acetate solution pH=7). Mass (ESI) M/e 504.18 (calculated $C_{11}H_{17}N_4O_{13}P_3$ 506.2), 1H NMR ($D_2O$, ppm) 7.73 (s, 1H), 6.34 (t, 1H), 4.72 (m, 1H), 4.21 (m, 3H), 2.37 (m, 2H), 1.92 (s, 3H).

Example 3

Thymidine mono-(4-acetamidobenzenesulphonyl) imino-triphosphate (chemical synthesis)

200 mg (0.99 mmol) 2-chloro-1,3,2-benzo-dioxaphosphorin-4-one (Aldrich) which was dissolved in 1.8 ml dimethylformamide and 150 µl pyridine was added at 0° C. to 240 mg (0.5 mmol) 2'-deoxy-3'-tert.butyldiphenylsilyl-thymidine under argon. The solution is stirred for 5 minutes at 0° C. and for 30 minutes at room temperature and subsequently a mixture of 2 ml of a 0.7 M solution of Bis(tributylammonium)-pyrophosphate in dimethylformamide and 280 µl triethylamine is added. After 1 hour at room temperature 360 mg (1.5 mmol) p-acetamidobenzenesulphonyl azide is added and stirred for a further hour at room temperature. 5 ml water is added to the reaction mixture and stirred for 15 minutes. The solvent is removed on a rotary evaporator and the residue is taken up in ethyl acetate and extracted with water. The non-aqueous phase is freed from water and the residue is suspended in tetrahydrofuran and 4 ml of a 1 M tetrabutylammonium fluoride solution in tetrahydrofuran is added and stirred for 2 hours at room temperature. The solvent is removed and the product is purified over a DEAE Sephadex A25 anion exchanger (eluant gradient: from 0.1 M ammonium acetate solution pH=7 in 120 minutes to 1 M ammonium acetate solution pH=7). Mass (ESI) M/e 678.0 (calculated $C_{18}H_{25}N_4O_{16}P_3S$ 678.4).

Example 4

Elongation Experiment

10 µl of a 2.5 µM 39 mer template desoxy-oligonucleotide and 5 µl of a 5 µM 20 mer primer desoxy-oligonucleotide complementary to the 3' portion of the template oligonucleotide were hybridized to each other in order to generate a partially double stranded DNA molecule according to standard methods.

Then, 20 µl of 1 mM 2'-Desoxythymidin α monocyaniminotriphosphat sodium salt, 10 µl ThermoPol Reaction Buffer BioLabs (M0257S) and 0.5 µl (2 U/µl) Vent (exo) DNA Polymerase BioLabs (M0257S) were added. Incubation of the set up was performed at 55° C. for 20 min.

Subsequently, the sample was purified over a Vivaspin 500-10.000 MWCO gel filtration spin column and desalted over a Vivaspin 500-5.000 MWCO gel filtration spin column.

For the extended primer desoxyoligonucleotide, mass spectrometry analysis revealed a molecular weight of (ESI) M/e 7403 corresponding to a calculated value of 7401.9.

What is claimed is:

1. An optionally labeled nucleotide, oligonucleotide, or polynucleotide having the structure

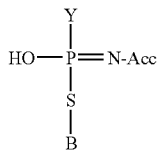

in which B is a 9-purinyl or 1-pyrimidinyl, S is an optionally 3'-substituted ribosyl moiety, Y is an OH, a monophosphate, a diphosphate, an oligonucleotide or a polynucleotide, in which Acc is an electron acceptor selected from the group consisting of (a) —CN and (b) —SO$_2$—R' in which R' contains one amino-substituted alkyl or one optionally substituted aryl.

2. The optionally labeled nucleotide, oligonucleotide, or polynucleotide according to claim 1 wherein the ribosyl moiety is a 1,5-disubstituted ribosyl, 1,5-disubstituted deoxyribosyl, or 1,5-disubstituted dideoxyribosyl.

3. The optionally labeled nucleotide, oligonucleotide, or polynucleotide according to claim 2, wherein the optional 3'-substituent is selected from the group consisting of H, OH, an O-protective group, a detectable label, a mononucleotide, a polynucleotide, and a solid phase.

4. A process for producing a nucleotide according to claim 1 comprising the step of reacting a trivalent phosphorus atom located at the 5' position of a nucleotide, the phosphorus atom having at least one protected hydroxyl group, with an azide of the structure

in which Acc is an electron acceptor selected from the group consisting of (a) —CN and (b) —SO$_2$—R' in which R' contains one amino-substituted alkyl or one optionally substituted aryl.

5. A process for producing a nucleotide according to claim 1 comprising the step of reacting a 5' phosphoramidite nucleoside with an azide of the structure

wherein Acc is an electron acceptor selected from the group consisting of (a) —CN and (b) —SO$_2$—R' in which R' contains one amino-substituted alkyl- or one optionally substituted aryl.

* * * * *